United States Patent [19]
Watson et al.

[11] Patent Number: 5,475,144
[45] Date of Patent: Dec. 12, 1995

[54] CATALYST AND PROCESS FOR SYNTHESIS OF KETENES FROM CARBOXYLIC ACIDS

[75] Inventors: P. C. Watson, Elkton, Md.; M. C. Libby, West Henrietta, N.Y.; M. A. Barteau, Wilmington, Del.

[73] Assignee: The University of Delaware, Newark, Del.

[21] Appl. No.: 255,348

[22] Filed: Jun. 8, 1994

[51] Int. Cl.$^6$ .................................................. C07C 45/89
[52] U.S. Cl. .................................... 568/301; 568/302
[58] Field of Search .................................... 568/301, 302

[56] References Cited

U.S. PATENT DOCUMENTS

| | | | |
|---|---|---|---|
| 1,602,699 | 10/1926 | Archer | 568/301 |
| 1,723,724 | 8/1929 | Clarke et al. | |
| 1,870,104 | 8/1932 | Dreyfus | 568/301 |
| 1,879,497 | 9/1932 | Rice | 568/301 |
| 1,975,663 | 10/1934 | Reid | 260/134 |
| 2,069,243 | 2/1937 | Graves et al. | 260/123 |
| 2,080,562 | 5/1937 | Eschenbach | 260/123 |
| 2,086,582 | 7/1937 | Steik | 260/123 |
| 2,108,829 | 2/1938 | Sixt et al. | 568/301 |
| 2,143,489 | 1/1939 | McAllister et al. | 260/550 |
| 2,175,811 | 10/1939 | Loder | 568/301 |
| 2,235,561 | 3/1941 | Nadeau et al. | 260/546 |
| 2,295,644 | 9/1942 | Fallows et al. | 568/301 |
| 2,305,652 | 12/1942 | Walters et al. | 260/550 |
| 2,383,863 | 8/1945 | Heuter | 260/550 |
| 2,393,778 | 1/1946 | Hull | 260/550 |
| 2,465,337 | 3/1949 | Miller et al. | 260/585.5 |
| 2,483,883 | 10/1949 | Corbiere | 260/585.5 |
| 2,513,825 | 7/1950 | Sorenson | 260/585.5 |
| 2,688,635 | 9/1954 | Eberts et al. | 260/547 |
| 2,820,058 | 1/1958 | Luke et al. | 260/585.5 |
| 3,136,811 | 6/1964 | Painter et al. | 260/546 |
| 3,161,683 | 12/1964 | Ciocchetti | 260/585.5 |
| 3,193,512 | 7/1965 | Ciocchetti | 252/451 |
| 3,366,689 | 1/1968 | Maeda et al. | 568/301 |
| 3,535,383 | 10/1970 | Rothman | 260/585.5 |
| 3,836,583 | 9/1974 | Matthias et al. | 260/585.5 |
| 4,455,439 | 6/1984 | Arnold et al. | 568/302 |

OTHER PUBLICATIONS

"Photodecomposition of Adsorbed Ethanoic Acid over Silica Gel Catalyst in a Flow System", Augugliaro, V. Palmisano, L., Schiavello, M. and Sclafani, A., J. Catal. 99, pp. 62–71 (1986).
"Site requirements of reactions on oxide surfaces", Barteau, M. A., J. Vac. Sci. Technol. A 11(4), pp. 2162–2168 (1993).
"The Interaction of Acetaldehyde and Acetic Acid with the ZnO Surface", Bowker, M., Houghton, H. and Waugh, K. C., J. Catal. 79, pp. 431–444 (1983).
"Ketene Polymers", Encyclopedia of Polymer Science and Technology, vol. 8, Interscience, New York, pp. 45–57 (1968).
"Unimolecular Reactions on Silica Surface", Brei, V. V., Gunk'ko V. M., Khavryuchenko, V. D. and Chuiko, A. A., Kinet. Catal. 31, 1019–1026 (1991).
"Study of Kinetics and Mechanisms of Some Unimolecular Reactions on Silica Surfaces", Brei, V. V., Gun'ko, V. M., Dudnik, V. V. and Chuiko, A. A., Langmuir 8, pp. 1968–1973 (1992).
"A Study of Surface Structures of Submicron Metal Oxides by Vanadium Tetrachloride as a Paramagnetic Probe", Chien, J. C. W., J. Am. Chem. Soc. 93, pp. 4675–4684 (1971).
"Hydroxyl Content in Silica Gel 'Aerosil'", Fripiat, J. J. and Uytterhoeven, J., J. Phys. Chem. 66, pp. 800–805 (1962).
"Surface heterogeneity in Silica Gel From Kinetics of Isotropic Exchange OH–OD", Fripiat, J. J., Gastuche, M. C. and Brichard R., J. Phys. Chem. 66, pp. 805–812 (1962).
"Comparative Study of the Surface Hydroxy Groups of Fumed and Precipitated Silicas. 4. Infrared Study of Dehydroxylation by Thermal Treatements", Gallas, J. P., Lavalley, J. C., Burneau, A. and Barres, O., Langmuir 7, pp. 1235–1240 (1991).
"Monomolecular Reactions on Silica Surface", Gun'ko, V. M., Brei, V. V. and Chuiko, A. A., Kinet. Catal. 32, pp. 91–96 (1991).
"The acidity of silica surfaces", Hair, M. L. in "Silicon Chemistry" (E. R. Corey, J. Y. Corey and P. O. Gaspar, Eds.), pp. 481–489, John Wiley & Sons, New York, (1988).
"Ketene From Acetic Acid", Hurd, C. D. and Martin, K. E., J. Am. Chem. Soc. 51, pp. 3614–3617 (1929).
"Catalytic Conversion of Acetic Acid on Metal Oxides", Imanaka, T., Tanemoto, T. and Teranishi, S. in "Proc. Int. Congr. Catal., 5th, Miami Beach, Fla., 1972" (J. W. Hightower, Ed.), 1, 163–172 (1973).
"Pathways for Carboxylic Acid Decomposition on $TiO_2$", Kim, K. S. and Barteau, M. A., Langmuir 4, pp. 945–953 (1988).
"Structure and Composition Requirements for Deoxygenation, Dehydration, and Ketonization Reactions of Carboxylic Acids on $TiO_2$(001) Single–Crystal Surfaces", Kim, K. S. and Barteau, M. A., J. Catal. 125, pp. 353–375 (1990).
"Ketenes and Related Substances", Kirk–Othmer Encyclopedia of Chemical Technology, pp. 874–893 Wiley–Interscience, (1978).
"Infrared and Gravimetric Study of an Aerosil and a Precipiatated Silica Using Chemical and H/D Exchange Probes", Morrow, B. A. and McFarlan, A. J., Langmuir 7, pp. 1695–1701 (1991).
"Catalytic Cracking of Acetic Acid to Acetic Anhydride", Padmanabhan, N., Deshpande, P. K. and Kuloor, N. R., I & EC Proc. Des. Dev. 7, pp. 511–516 (1968).
"Surface Chemistry of Oxides", Parfitt, G. D., Pure & Appl. Chem. 48, pp. 415–418 (1976).
"Formation of Ketenes by Reaction of Carboxylic Acids over Alkali Metal–Exchanged Zeolites", Parker, L. M., Bibby, D. M. and Miller, I. J., J. Catal. 129, pp. 438–446 (1991).

(List continued on next page.)

Primary Examiner—James H. Reamer
Attorney, Agent, or Firm—Connolly & Hutz

[57] ABSTRACT

This invention relates to a process of manufacturing ketenes, more particularly, a process for manufacturing ketenes by gas phase dehydration of carboxylic acids. The catalyst used in this process consists of a high surface area silica of at least 100 $m^2$/gram.

19 Claims, 5 Drawing Sheets

OTHER PUBLICATIONS

"The Decomposition of Ethanol, Propanol and Acetic Acid Chemisorbed on Magnesium Oxide", Parrott, S. L., Rogers, Jr., J. S. and White, J. M., Appl. Surf. Sci. 1, pp. 443–454 (1978).

"Dehydration of Carboxylic Acids on the MgO(100) Surface", Peng, X. D. and Barteau, M. A., Catal. Lett. 7, pp.395–402 (1990).

"Reaction Pathways and Intermediates in the Decomposition of Acetic and Propionic Acids on the Polar Surfaces of Zinc Oxide", Vohs, J. M. and Barteau, M. A., Surf. Sci. 201, pp. 481–502 (1988).

"Mechanism for the thermal decomposition of the salts of carboxylic acids", Yakerson, V. I., Izv. Akad. Nauk SSSR, Otd. Khim Nauk, pp. 1003–1011 (1963).

"Concentration of Hydroxyl Groups on the Surface of Amorphous Silicas", Zhuravlev, L. T. Langmuir 3, pp. 316–318 (1987).

"The Recovery of Aluminum Chloride from Sodium Tetrachloroaluminate", Batha, H. Dean, Whitney, E. Dow and Faust, J. Philip, Chem. & Ind., pp. 422–423 (1966).

"Synthesis of Ketene and Higher Ketenes from Carboxylic Acids on Silica", Libby, Mark C., Aug. 1992.

CATALYST AND PROCESS FOR SYNTHESIS OF KETENES FROM CARBOXYLIC ACIDS

BACKGROUND OF THE INVENTION

1. Field of the Invention

This invention relates to a novel process of manufacturing ketenes.

2. Description of Related Art

Ketenes are highly reactive chemical intermediates of the general form RR'C=C=O. Ketenes find application as powerful acylating agents for a range of compounds. Alkyl ketene dimers (AKD) are produced from long chain ($C_8$–$C_{32}$)fatty acids for use as paper sizing agents.

While there exist a variety of routes to ketenes, these do not generally involve heterogeneous catalysis. Low molecular weight ketenes are produced by thermal pyrolysis of carboxylic acids or ketones at 600°–800° C. (Encyclopedia of Polymer Science and Technology, Vol. 8, Interscience, New York, (1968), p. 45, Rice, F. O., Greenberg, J., Waters, C. E., Vollrath, R. E., J. Am. Chem. Soc. 56, 1760 (1934), Hurd, C. D. and Roe, A., J. Am. Chem. Soc. 61, 3355 (1939), Hurd, C. D. and Martin, K. E., J. Am. Chem. Soc. 51, 3614 (1929), Bamford, C. H. and Dewar, J. S., J. Chem. Soc., 2877 (1949) and Guenther, W. B. and Walters, W. D., J. Am. Chem. Soc. 81, 1310 (1959)). Higher molecular weight ketenes are produced by dehalogenation of α-halo acyl halides or dehydrohalogenation of acyl halides with tertiary amines as disclosed in U.S. Pat. No. 2,383,863 issued to R. Heuter and U.S. Pat. No. 3,535,383 issued to E. S. Rothman. None of these routes enjoys the efficiency of a catalytic process. The dehalogenation-based processes are multistep organic syntheses which utilize hazardous reagents, e.g. phosgene, and solvents, and yield undesirable by-products. Thus efficiency, safety and waste minimization imperatives all favor the development of a one-step catalytic process.

Gun'ko and coworkers (Brei, V. V., Gun'ko, V. M., Khavryuchenko, V. D., Chuiko, A. A.,, Kinetics and Catalysis 31, 1019 (1991), Brei, V. V., Gun'ko, V. M. Dudnik, V. V., Chuiko, A. A., Langmuir, 8, (1992), and Gun'ko, V. M., Brei, V. V., Chuiko, A. A., Kinetics and Catalysis 32, 91 (1991)) observed the formation of ketene in temperature programmed desorption "TPD" experiments in which acetic acid and acetyl chloride were employed to synthesize acetoxysilyl groups on aerosils.

U.S. Pat. No. 3,366,689 issued to Maeda et al. describes a process for manufacturing ketenes by contact dehydration for aliphatic carboxylic acids having 3 to 6 carbon atoms with a silica catalyst having a specific surface area of less than 100 m²/g. and at a temperature of 400°–900° C. The silica catalyst may be diatomaceous earth, pumice, acid clay, kaolin, aluminum silicate, magnesium silicate or silica-boric oxide.

U.S. Pat. No. 2,175,811 issued to Loder describes a process for preparation of ketene which comprises thermally decomposing lower aliphatic monocarboxylic acid esters in the vapor phase at 500°–1000° C. in contact with a catalyst which can be silica gel supporting a promoter such as phosphoric acid or boron oxide.

U.S. Pat. No. 2,295,644 issued to Fallows et al. describes a process for manufacturing ketene and acetic anhydride by thermal dehydration of acetic acid vapors in the presence of a catalyst by passing the vapors at 500°–1000° C. over pumice with zinc oxide or cadmium oxide deposited on the surface.

U.S. Pat. No. 1,870,104 issued to Dreyfus describes a process for the manufacture of ketene, acetic acid or acetic anhydride or mixture thereof which comprises passing vapors of acetic acid and acetaldehyde at 500°–600° C. over a catalyst selected from a group which includes pumice.

U.S. Pat. No. 2,108,829 issued to Sixt et al. describes a catalytic process for producing ketene which comprises subjecting acetic acid vapors containing acetic anhydride forming catalyst to heating at a temperature between 500°–1000° C. under partial vacuum and immediately separating ketene from the other components. Solid catalysts, such as pea size "carborundum" coated with sodium metaphosphate, may be used (Example 1).

A BRIEF SUMMARY OF THE INVENTION

It is object of this invention to have a more efficient process for producing ketenes.

It is another object of this invention to operate at lower temperatures then described above.

It is another object of this invention to reduce the byproduct formation.

It is another object of this invention to have a process that can produce ketenes in a one-step catalytic process.

It is still a further object of this invention to have a safer process which also involves less waste formation than other processes such as (1) thermal pyrolysis of carboxylic acids or ketones, and (2) dehalogenation of α-halo acyl halides, and (3) dehydrohalogenation of acyl halides with tertiary amines.

The invention relates to a process for the production of ketenes comprising dehydration of a carboxylic acid in the presence of a catalyst which comprises silica having a high surface area of at least 100 m²/grams.

This catalyst can operate at temperatures substantially lower (by 200–300K) than those at which conventional processes for ketene production by thermal pyrolysis of carboxylic acids, ketones, or esters are operated.

The ketenes manufactured according to the claimed process are useful in areas such as but not limited to, acylating agents for pharmaceutical and sizing agents (intermediates for alkyl ketene dimers and multimers).

DESCRIPTION OF THE PREFERRED EMBODIMENT

This invention relates to a process for the production of ketenes by catalytic dehydration of carboxylic acids. This catalyst comprises high surface area silica of at least 100 m$^2$/gram and preferably about 120 to about 800 m$^2$/gram and more preferably of at least about 380 m$^2$/g containing hydroxyl groups on its surface at concentrations of 0 to 8/nm$^2$, preferably about 0.5 to 8/nm$^2$ and most preferably from about 0.5 to about 3/nm$^2$. The catalyst can contain other ingredients such as but not limited to Ni, Na, Li, Cl, Fe, Cu, Ti, Mg, Ca or K. Selectivities for production of ketenes such as, but not limited to $C_2$–$C_{32}$ ketenes, preferably from $C_2$–$C_{22}$ and most preferably from $C_2$–$C_5$ ketenes, from at least about 35 %, preferably from at least 35 % up to about 90% at carboxylic acid conversions of about 30 to about 100% have been achieved in a flow reactor containing this catalyst.

One of the ways to prepare the catalyst of this invention can be by pretreating by a step of hydration with water or steam to increase the amount of hydroxyl groups forming on the surface of the catalyst. The water can be added in an excessive amount preferably in the amount to achieve incipient wetness. The catalyst then can be heated to temperatures above the boiling point of water to allow some of the hydroxyl groups to be removed. The pretreating step allows for the desired amount of hydroxyl to be present. The catalyst can be produced by other exposure to water or vapor and/or temperature treatments to achieve the desired hydroxyl level for the active catalyst.

The ketenes can be produced in a reactor system. The reactor system can be batch or continuous. A continuous system is however preferred. The ketenes can produced in a reactor, preferably a flow reactor containing this catalyst which can be at a temperature of at least about 600 K. and preferably from about 700 K. to about 1000 K. and more preferably from about 700 K. to 750 K. The ketenes can be straight chain or branched chain. The pressures could be at an elevated pressure or run in a vacuum.

This temperature according to this invention, can be substantially lower (by 200–300 K.) than those at which conventional processes for ketene production by thermal pyrolysis of carboxylic acids, ketones, or esters are operated.

EXPERIMENTAL

The reactor system used in these experiments has been described in detail in Kim, K. S. and Barteau, M. A., Langmuir 6, 1485 (1990), Idriss, H., Kim, K. S., Barteau, M. A., J. Catal. 139, 119 (1993), Libby, M. C., M. Ch.E. Thesis, University of Delaware (1992) and Libby, M. C., Watson, P. C. and Barteau, M. A., "Synthesis of Ketenes with Oxide Catalyst" submitted for publication to Industrial and Engineering Chemistry Research in March 1994 which are hereby all incorporated into reference. The reactor was a quartz U-tube containing a porous glass frit on which the catalyst sample rested. The reactor was suspended in a cylindrical furnace for temperature regulation. Gas flow to the reactor was controlled by mass flow controllers for flow rates of 0 to 100 cc/min, or by use of a rotameter at higher flow rates (up to 450 cc/min). An inert gas such as a high purity helium (grade 5) was used as the carrier gas in all experiments; for adsorption and steady state reaction experiments the carrier gas was passed through a bubbler containing the carboxylic acid of choice. The exit stream from the reactor was sampled with a differentially pumped UTI 100C quadruple mass spectrometer. The pressure was reduced from 1 atmosphere to ca. 10$^{-6}$ torr at the mass spectrometer with a differentially pumped UTI Atmospheric Pressure Sampling Module. The mass spectrometer can be controlled by a computer and multiplexed in order to monitor up to 100 masses concurrently during temperature programmed and steady state reaction experiments. The computer can also control the reactor temperature, measured with a thermocouple inserted into the catalyst bed.

Three classes of silica samples were used in these experiments. Chromatographic grade silica (commercially available from BDH) and both hydrated and non-hydrated fumed silicas (such as commercially available silicas from Cabot Corporation, Cab-O-Sils L-90, M-5, HS-5 and EH-5). The hydrated samples were mixed with water, preferably in excess, dried at about 80° C. in air and then powdered with a metal spatula.

Then temperature programmed reaction experiments were carried out as follows. The catalyst sample was weighed and typically about 30 to about 100 mg were placed in the reactor, which was then reconnected to the flow system. The powder was then heated under a flowing gas such as a high purity helium (30 cc/min) to remove adsorbed water and any volatile contaminants. The sample was held at the chosen pretreatment temperature for a minimum of about two hours. The pretreatment temperature for most of the experiments described below was about 750K., although this was varied from about 573 to about 973 K. in a few experiments in order to evaluate the influence of pretreatment temperature on catalyst performance. At the end of the pretreatment, the catalyst was cooled to room temperature in a flowing gas such as helium. Reactants were adsorbed by diverting the helium flow through the bubbler ahead of the reactor. The bubbler was heated when using higher molecular weight, less volatile reactants to achieve a minimum reactant vapor pressure of about 10 torr. Saturation of the catalyst sample with the absorbate typically required exposure times up to about 20 minutes, as determined using the mass spectrometer to monitor the recovery of the reactant partial pressure in the exit stream from the reactor to the level observed when bypassing the reactor. After completion of the reactant exposure, the reactor was purged with a flow of gas, preferably an inert gas such as helium, for about one hour. At that point temperature programming was initiated at a rate of about 30 K./minute up to a maximum temperature of about 900 K., monitoring the desorbing products with the mass spectrometer.

Steady state reaction experiments followed a similar procedure. After the initial catalyst pretreatment, the catalyst was maintained at the reaction temperature. Initially the bubbler containing the carboxylic acid was bypassed, and the background signals were determined for all fragments to be monitored with the mass spectrometer. Next, by switching the appropriate valves, the gas flow was diverted through the bubbler and sampled with the mass spectrometer while bypassing the reactor. This permitted the determination of the relative acid concentration in the feed, as well as the direct determination of reactant fragmentation pattern in the mass spectrometer. After these signals reached constant level, the flow was directed through the reactor. The decrease in the reactant signal and the increase in the product signals were monitored continuously with the mass spectrometer. Steady state was typically reached in less than about 30 minutes and the maintenance of activity was monitored for about 1 hour up to more than 20 hours in a few experiments.

Analysis of the products required deconvolution of overlapping mass spectrometer fragmentation patterns for the various reactants and products. This was accomplished as follows. The signals corresponding to mass fragments of the parent acid, $CO_2$, and water were readily identifiable and their contributions were subtracted from the observed product fragments. The crucial distinction to be drawn was between the fragments of the ketene vs. ketone products. For symmetric ketones ($RCH_2$—CO—$CH_2R$) the fragment which gives rise to the most intense mass spectrometer signal is typically the acyl group ($RCH_2CO$). The mass-to-charge (m/q) ratio of this group is one mass unit higher than that of the corresponding ketene (RCH=C=O) parent mass. Experimental values of these fragmentation patterns were measured for the ketones produced in these experiments, and the contribution of ketone fragmentation to the signal at the m/q value corresponding to the ketene parent mass could therefore be determined. In all cases the intensity ratio of ketone-derived $RCH_2CO$/RCHCO groups was greater than 10; thus lower values of this ratio among the reaction products provide a clear fingerprint for the formation of ketenes.

Quantification of product ratios requires the application of sensitivity factors which take into account ionization cross section, fragmentation, transmission, etc. These are easily computed if the fragmentation pattern of the molecule is obtained, as was feasible for all products in this study except the ketenes. Sensitivity factors for the ketenes were calculated as follows. The signals for the parent mass of the ketene and those at m/q values 1 and 28 mass units less (the principal ketene fragmentation channels) remaining after assignment of all contributions from carboxylic acid and ketone fragmentation, were assigned to the ketene product. For ketene and dimethyl ketene, these could be checked against known literature values Stenhagen E. (ed), Atlas of Mass Spectral Data, Vol. I, II, III, John Wiley & Sons, New York, 1969). The ratio of these signals was assumed to reflect the fragmentation pattern of the appropriate ketene, and the relative mass spectrometer sensitivity to ketene was calculated on that basis. Qualitative confirmation of the production of ketene was provided by separate experiments in which the gaseous product was examined by infrared spectroscopy or condensed with cyclohexanol to form cyclohexyl acetate and examined by NMR spectroscopy and gas chromatography (Libby, M. C., M. Ch.E. Thesis, University of Delaware, 1992).

The thermogravimetric analyses (TGA) were carried out using a mass analyzer such as a TEOM Series 1500 Pulse Mass Analyzer (from Rupprecht & Patashnick Co., Inc.). For these experiments, the silica powder was sandwiched between plugs of quartz wool at the end of a 16 cm long, hollow tapered glass element. This tapered element was suspended in a stainless steel tube, heated externally. The end of the glass element where the powder bed is located is flared to approximately 4 mm ID. A stainless steel cap was used to secure the bed contents. The feed gas was passed through the tapered element, with a sweep gas flowing in the surrounding annular space. A gas such as a high purity helium (grade 5) at 30 cc/min. and 15 cc/min. was used for the reactor flow-through and sweep gas, respectively. Silica sample masses used for these experiments were between 30 and 100 mg. A controlled heating and cooling rate of 7 K./min. was used for the TGA experiments.

Results of the Experiments were as follows:

A. Temperature Programmed Desorption

Temperature programmed desorption of acetic acid from silica produces ketene. Two principal desorption channels were observed. The lower temperature (450 K.) peaks are characteristic of acetic acid desorption, and the relative intensity of the peaks at this temperature for different m/q values were consistent with the fragmentation pattern of acetic acid. The higher temperature peaks (at 740–750 K.) are those of the various reaction products, $CO_2$, acetone, and ketene, and resemble those produced by decomposition of surface acetate intermediates on a variety of other oxides. Silica is distinguished by its high selectivity for ketene production from adsorbed acetates. The mass spectrometer fragmentation pattern for acetone exhibits a ratio of fragments at m/q=43 to 42 of 10:1; in contrast, the signal for m/q= 42 at 750 K. was larger than that for m/q=43. Thus more than 90% of the m/q=42 peak at 750 K. must be due to the production of ketene. Substantial signals for m/q=14 and 41, the other principal fragments of ketene in the mass spectrometer were also observed for the 750 K. peak. Quantitative calculation of the ketene selectivity, defined as the fraction of the carbon among the products present as ketene, produced a value of 0.37±0.07 from a number of repetitions. In contrast, no other oxide tested in similar TPD experiments, including MgO, $TiO_2$, ZnO, $MgAl_2O_4$, -$\gamma$-$Al_2O_3$, $V_2O_5$, and HZSM-5 (Si/Al=900), produced ketene with a selectivity greater than 7%, and most were substantially less selective.

Both the activity and selectivity of the BDH silica gel for ketene production by acetic acid TPD were found to depend on the temperature at which the catalyst sample had been heated prior to acetic acid exposure at 300 K. Both ketene yield and selectivity decreased monotonically as the pretreatment temperature was increased from about 573 to about 973 K. This variation likely reflects changes in the population and type of surface hydroxyl groups. A pretreatment temperature of 750 K. was chosen for all subsequent experiments. While this does not produce the highest ketene yields from BDH silica for acetic acid TPD, elevated pretreatment temperatures were essential for steady state catalysis experiments. The TPD results demonstrated the onset of product desorption at about 700 K., thus attempts to carry out this reaction at steady state require operating temperatures at about this level or higher, and catalyst pretreatment at temperatures below the onset temperature for carboxylate reaction to ketene would therefore be pointless.

Higher molecular weight carboxylic acids also produce ketenes of the corresponding carbon number in TPD experiments on silica. The results of TPD experiments with propionic acid ($CH_3CH_2COOH$), butyric acid ($CH_3CH_2CH_2COOH$), isobutyric acid (($CH_3)_2CHCOOH$) and valeric acid ($CH_3CH_2CH_2CH_2COOH$), all resembled that for acetic acid TPD: a low temperature peak corresponding to desorption of the unreacted acid followed by carboxylate decomposition to ketenes, ketones and carbon oxides above 700 K. The ketene products from these acids were methyl ketene ($CH_3CH$=C=O), ethyl ketene ($C_2H_5CH$=C=O), dimethyl ketene (($CH_3)_2C$=C=O) and propyl ketene ($C_3H_7CH$=C=O), respectively. The ketone products result from coupling a pair of carboxylates, and contain 2n-1 carbon atoms when produced from n-carbon carboxylic acids. Thus the ketone products were 3-pentanone, 4-heptanone, 2,4-dimethyl-3-pentanone, and 5-nonanone, respectively, for the carboxylic acids reacted above. Because of the high mass of both ketene and ketone products of higher carboxylic acids, their mass spectrometer signals are less intense than those of their smaller counterparts produced from acetic acid. However taking into account both product fragmentation patterns and the decreasing transmission of the mass spectrometer for higher m/q values in the calculation of mass spectrometer sensitivity factors, one finds that the yields of dehydration and coupling products do not exhibit a strong dependence on reactant carbon number. As shown in Table 1, ketene selectivities in TPD experiments on BDH silica were between 35 and 60% for all of the linear $C_2$–$C_5$ carboxylic acids examined, and that for dimethyl ketene from isobutyric acid was even higher, 85%.

TABLE 1

TPD Product Distribution for Carboxylic Acid Conversion on BDH Silica

| Carboxylic Acid | Product Yield[a] | | | Ketene[b] Selectivity |
|---|---|---|---|---|
| | Ketene | Ketone | $CO_2$ | |
| Acetic | 1.0 | 0.5 | 1.9 | 0.37 |
| Propionic | 2.5 | 1.1 | 2.5 | 0.48 |
| Butyric | 2.0 | 0.1 | 4.9 | 0.59 |
| i-Butyric | 4.5 | 0.04 | 2.9 | 0.85 |
| Valeric | 9.0 | 3.5 | 7.7 | 0.53 |

[a]Product yields corrected for mass spectrometer sensitivity factors and normalized to the ketene product from acetic acid.
[b]Based on carbon content.

These results suggest that high molecular weight ketenes can indeed be produced by this route.

B. Steady State Catalysis

Figure 1:
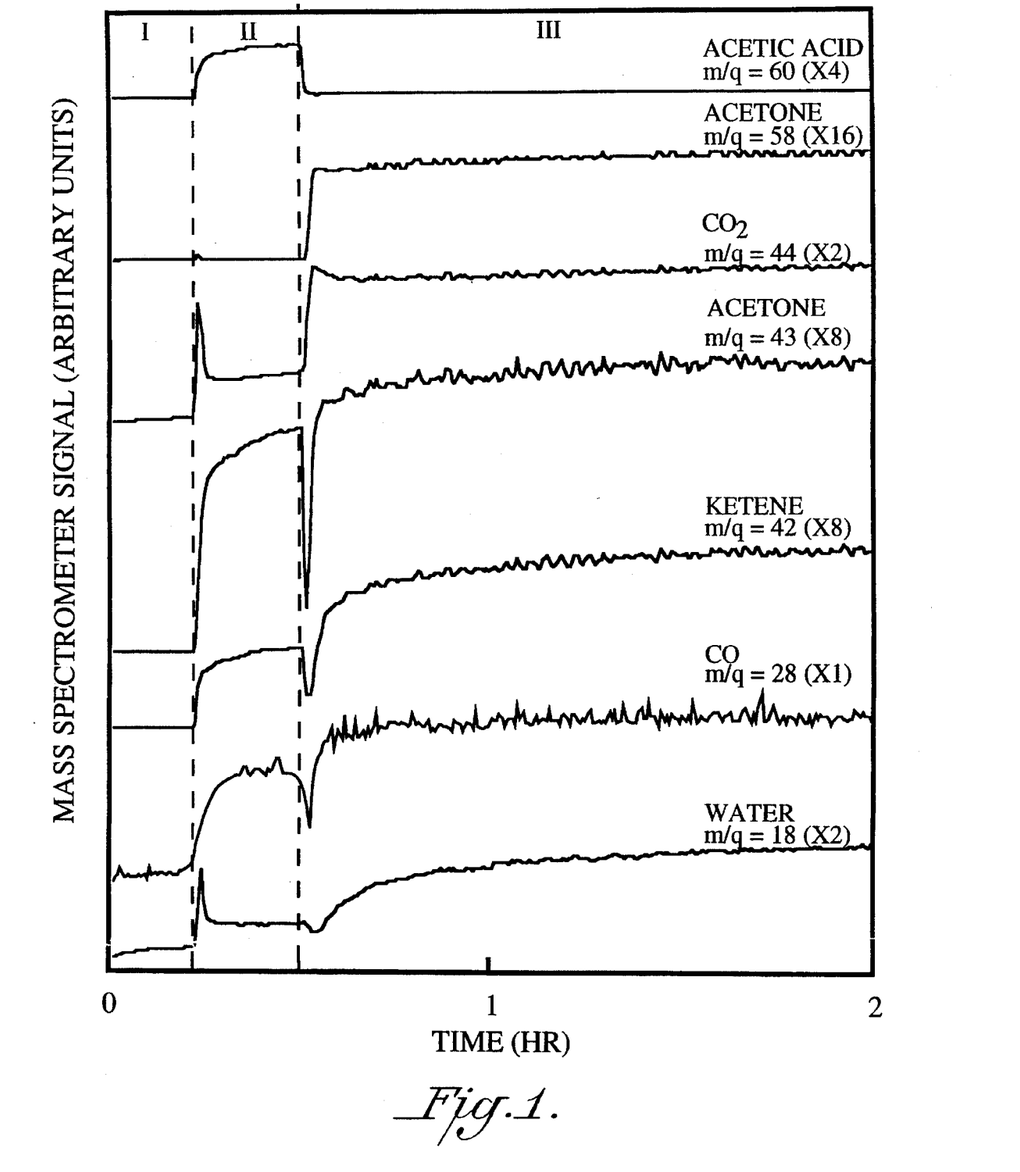
FIG. 1 is a graph of a mass spectrometer signal over time of a steady state reaction of acetic acid on BDH silica.

The silicas employed in the TPD experiments were active, stable catalysts for ketene production when operated at temperatures corresponding to the ketene peaks observed in TPD. FIG. 1 illustrates an example of steady state run at high acetic acid conversion. In this example, 100 mg of BDH silica was pretreated in flowing gas such as helium at about 750 K. and the reaction of acetic acid was carried out at 750 K. for up to 3.5 hours. The mass spectrometer traces in FIG. 1 are divided into three segments to illustrate the experiment sequence. In the first segment (Region 1), the helium carrier gas bypassed both the acetic acid bubbler and the reactor to permit determination of the background signal from the mass spectrometer. After several minutes, acetic acid was introduced into the gas stream via the bubbler and the signal for acetic acid came to steady state after about 20–25 minutes (Region II). At that time, the reactant flow was switched from bypass to the reactor (Region III). As can be seen in the topmost trace of FIG. 1, the acetic acid level decreased rapidly upon contact with the catalyst, reaching steady state in less than 10 minutes. During the time the acetic acid bypassed the reactor (Region II), the intensity increased for all masses represented in the cracking pattern of acetic acid. M/q=60 was used to monitor acetic acid, since none of the expected products would give rise to this mass. To correct the product signals for contributions from acetic acid cracking in the mass spectrometer, baselines for each mass were constructed. This height of the baseline in each case was determined by multiplying the m/q=60 signal during the reaction by the mass spectrometer cracking ratios obtained during the previous bypass phase of operation. No correction was necessary for the experiment illustrated in FIG. 1, as the acetic acid conversion was essentially 100%. As expected from the TPD results, there was a net increase in the signals in Region III for m/q=18 (water), 28 (carbon monoxide), 42 (ketene), 43 and 58 (acetone), and 44 (carbon dioxide). Other products, including acetaldehyde and hydrocarbons, were checked for but not found.

A mass balance on the carbon content was carried out by measuring the intensity decrease for acetic acid due to reaction and comparing it with the sum of the product yields. Ketene (m/q=42) and carbon monoxide (m/q=28) were corrected for cracking of acetone, as acetone was formed in Region III as well. The carbon balance was performed by multiplying the intensity difference due to reaction by the appropriate mass spectrometer sensitivity factor (1 for CO, 1.5 for $CO_2$, 2.4 for ketene, 7.5 for acetone at m/q=58, and 6 for acetic acid) and the carbon number (the number of carbon atoms in the molecule) for the reactant and products. In the experiment shown in FIG. 1, the carbon content of the products computed in this fashion was within 10% of the carbon provided by the reactant, acetic acid. This deviation reflects the accuracy limit of the computed mass spectrometer sensitivity factors.

Steady state experiments could be carried out for up to 20 hours without loss of activity of the catalyst. At the end of the experiment, especially at the higher temperatures, the catalyst had darkened, most likely due to carbon deposition. However, the carbon did not appear to decrease the activity or selectivity of the catalyst. The carbon on the catalyst could be removed by heating the catalyst in air or oxygen for several hours.

Figure 2:
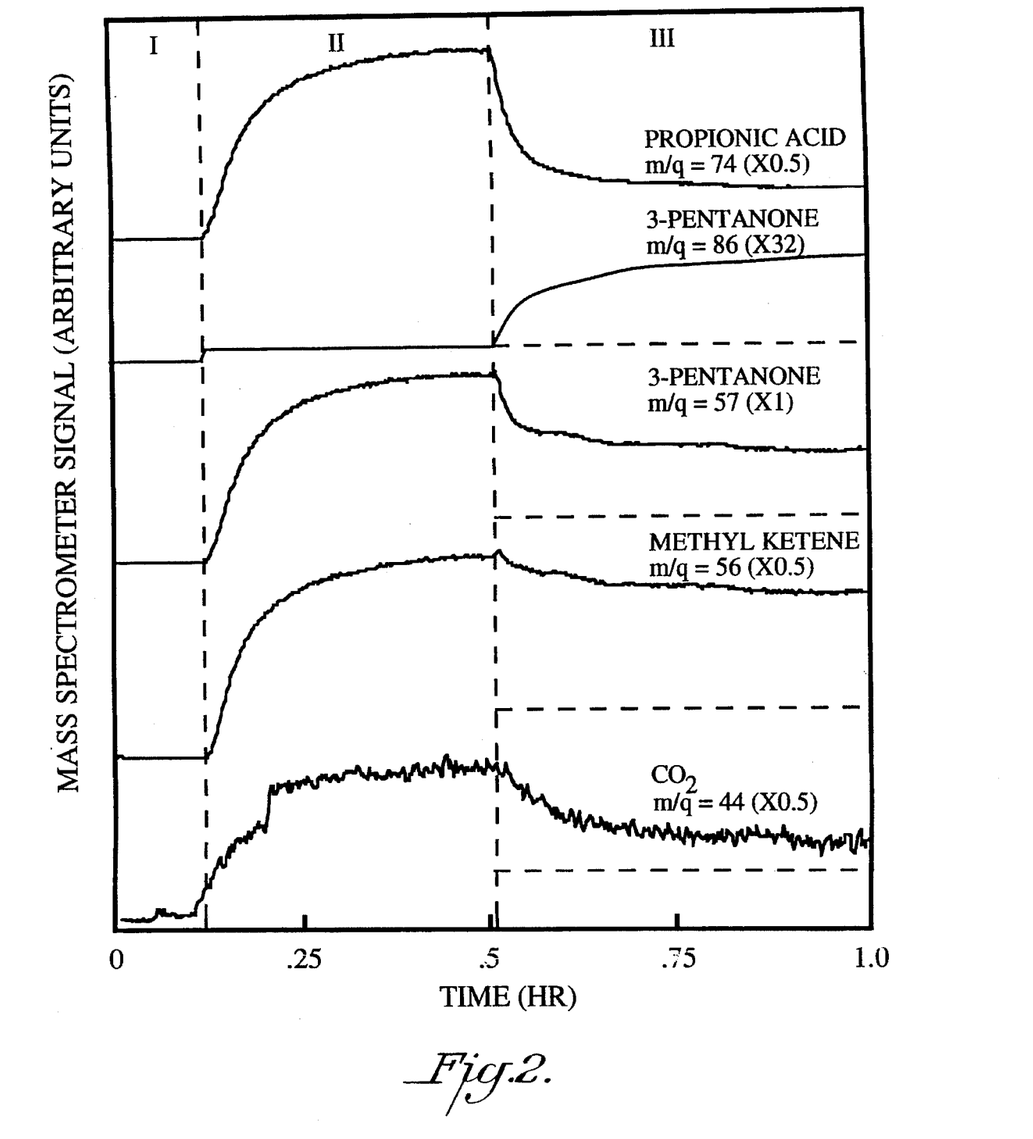
FIG. 2 is a graph of a mass spectrometer signal over time of steady state reaction of propionic acid on BDH silica.

In order to compare ketene selectivities for the various $C_2$–$C_5$ carboxylic acids at lower conversions, the carrier gas flow rate was increased to 450 cc/min and the catalyst mass and reactor temperature were reduced to 30 mg and 700° K., respectively. An example of the steady state conversion of propionic acid under these conditions is shown in FIG. 2. The broken horizontal lines in Region III represent the base lines contributed by cracking of the unreacted acid in the mass spectrometer, determined as described above. For the experiment in FIG. 2, the conversion of propionic acid was 63% with a selectivity to methyl ketene of 68%.

Figure 3:
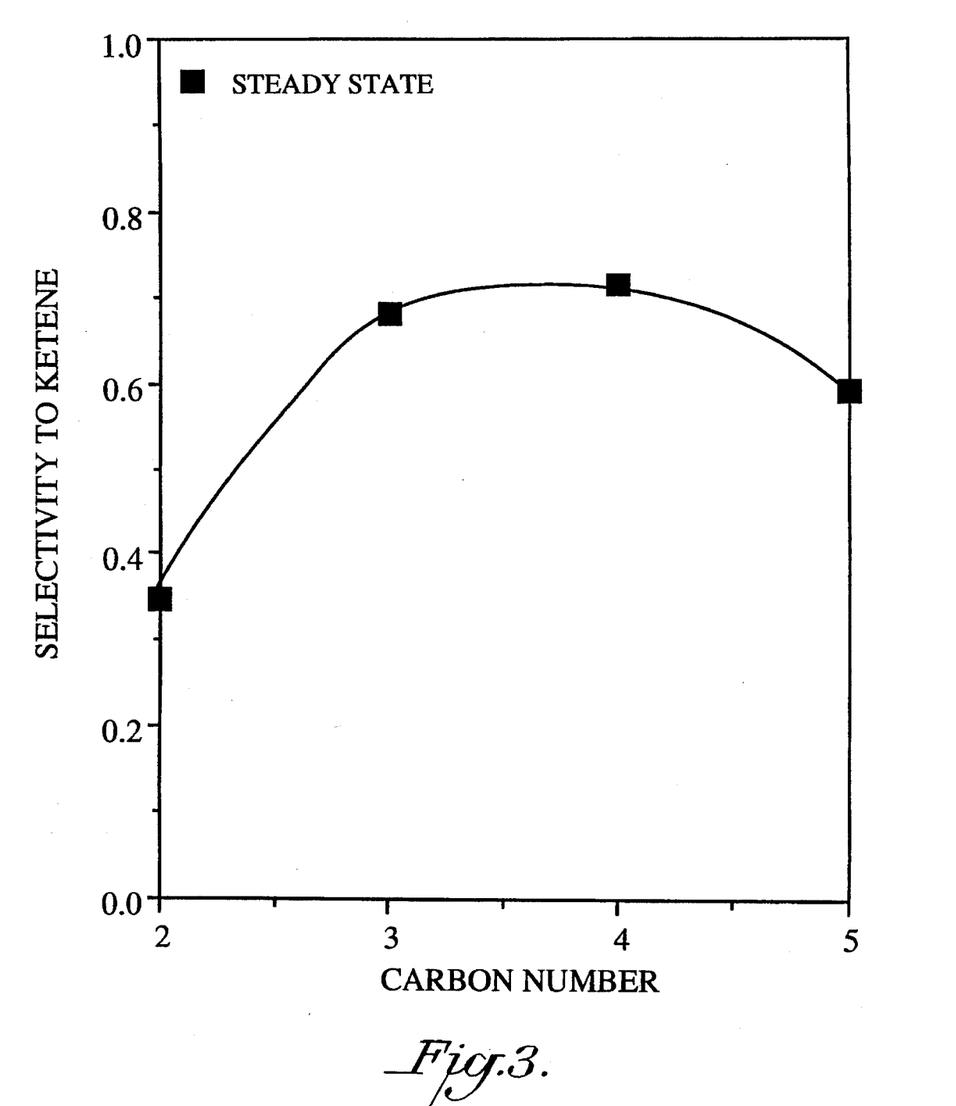
FIG. 3 is a graph of selectivity to ketene versus carbon number for steady state operation.

FIG. 3 compares the ketene selectivities obtained for all $C_2$–$C_5$ carboxylic acids examined, for the steady state conditions of FIG. 2. These results demonstrate that the significant levels of ketene production that can be achieved by catalytic dehydration of carboxylic acids with silica. There is no obvious decrease in ketene selectivity with carbon number, indicating that this process can be useful for the production of even higher molecular weight ketenes. The results of FIG. 3 and Table 1 establish the correspondence of selectivities between steady state and temperature programmed experiments, and establish the latter as a valid catalyst screening tool for this process. Temperature programmed desorption of acetic acid was therefore employed as the principal method for probing activity and selectivity in the catalyst characterization and optimization studies described below.

C. Catalyst Characterization and Optimization

The patent of Maeda et al. teaches that silicas with surface areas in excess of 100 $m^2$/g are unselective for ketene production. The results presented above are in clear conflict with Maeda et al.; the BDH silica employed in our invention (BET surface area=650 $m^2$/g) is clearly capable of producing ketene at the 40% yields claimed by the Maeda patent (for low surface area materials). However, in order to investigate the influence of surface area and other factors further, it was necessary to choose a family of silicas whose properties varied in a known or measurable fashion. A series of fumed silicas (Cab-O-Sils) were chosen for this purpose. These materials are of higher purity than the chromatographic grade silica above, and a series of experiments in which the Cab-O-Sils were doped with small amounts of metals were carried out to ensure that the performance of the BDH silica did not arise from impurities. Loading the fumed silicas at a level of about 0.05 to about 0.1 wt. % or higher with Fe, Cu, Ti, Mg, Ca, or K was found to provide no clear benefit and to decrease ketene selectivity and yield in most cases, and is not considered further here. Rather, properties such as surface area, and extents of catalyst hydration and dehydroxylation appear to be crucial factors, and the evaluation of these for Cab-O-Sil samples is considered below.

Figure 4A:
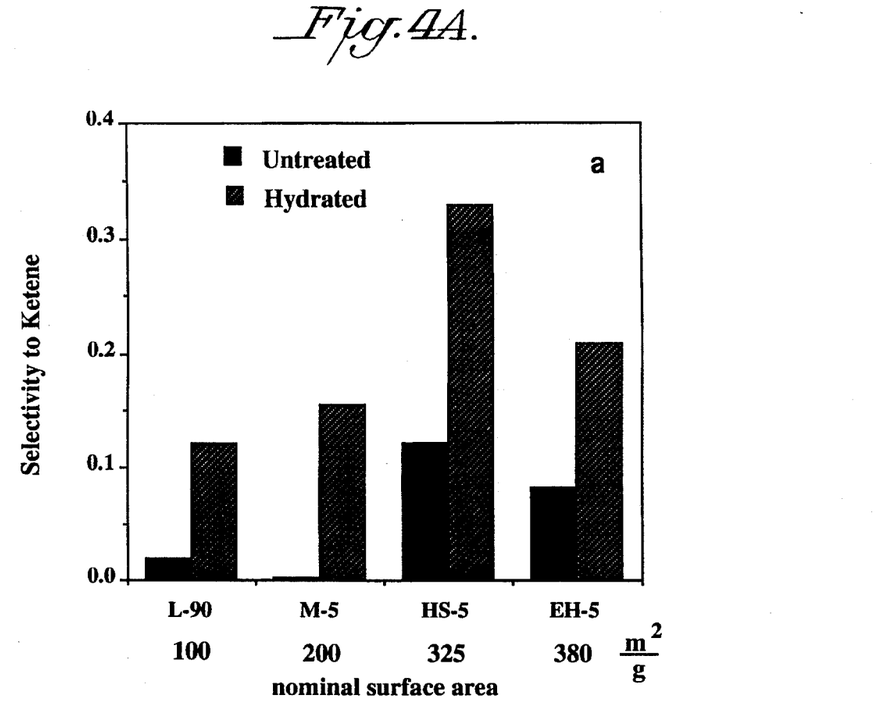
FIG. 4(a) is a graph of ketene selectivity versus surface area for hydrated and untreated Cab-O-Sil.
Figure 4B:
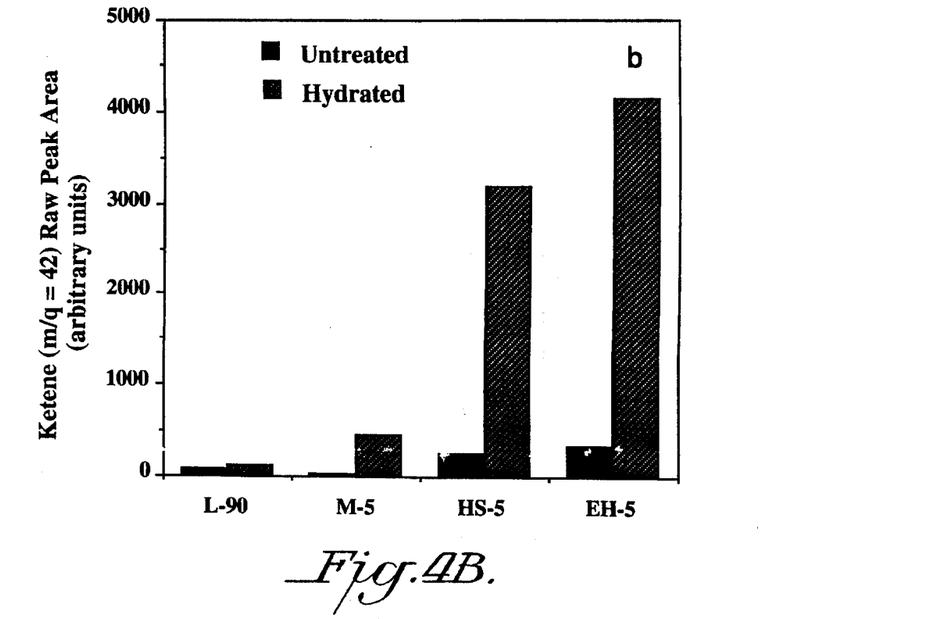
FIG. 4(b) is a graph of mass spectrometer signal (proportional to ketene yield) from acetic acid TPD as a function of Cab-O-Sil surface area and hydration.

Substantial performance differences were observed between nonhydrated and hydrated Cab-O-Sil powders. Hydrated samples were wetted with water, dried, and powdered as described above. Untreated (non-hydrated) samples were used as supplied by the manufacturer. Selectivities and yields to ketene were substantially higher for the hydrated samples. FIG. 4 compares TPD results (as a diagnostic test of the effects from surface area and hydration) from untreated and hydrated samples of several grades of Cab-O-Sil. FIG. 4 emphasizes the importance of hydrating the samples. The selectivity to ketene is shown in FIG. 4a. The yield of ketene (which is proportional to the uncorrected peak area for m/q=42) is shown in FIG. 4b. Both hydrated and untreated samples were calcined at 750 K. prior to exposure to acetic acid, following the procedure described above. The ketene activity and selectivity exhibited a more than 10-fold increase for the hydrated samples compared to the untreated samples. This difference in catalyst performance is attributed to differences in surface hydroxyl population and is discussed in detail below. The selectivities of FIG. 4(a) are characteristic of TPD experiments.

The influence of surface area on ketene yield was demonstrated by using various Cab-O-Sil fumed silicas with nominal surface areas between 100 and 380 $m^2/g$. TPD product yields for the four fumed silicas are shown in FIG. 4b. These data clearly show that, for the hydrated samples, ketene yield increases with increasing silica surface area. Although this relationship was not strictly linear, it is quite clear that ketene production is enhanced on catalysts with surface areas greater than 100 $m^2/g$, counter to the conclusions of Maeda et al (U.S. Pat. No. 3,366,689). The ketene selectivity of the various hydrated Cab-O-Sils did not show a monotonic dependence on surface area, as shown in FIG. 4a, but it should be recalled that the highest surface area material examined, the BDH silica, also produced ketene from acetic acid with the highest selectivity. Thus we found no evidence for a deleterious effect of silica surface area on either ketene selectivity or yield, with a clearly beneficial effect on the latter.

Figure 5:
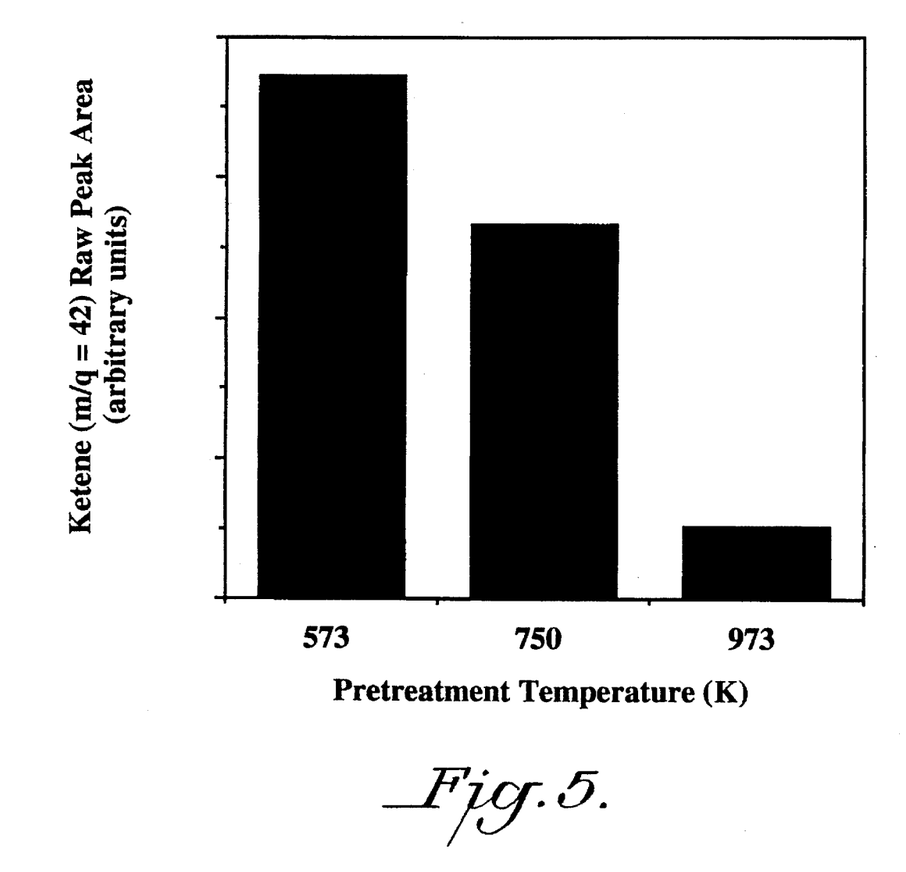
FIG. 5 is a chart showing the variation of ketene signal for acetic acid TPD vs. pretreatment temperature of hydrated Cab-O-Sil.

In order to further characterize the Cab-O-Sil EH-5, the base case material examined for this section of work, pretreatment temperature was varied. The ketene yields for hydrated Cab-O-Sil EH-5 samples using a lower than normal (573 K.) and higher than normal (973 K.) temperature for the two-hour pretreatment in flowing helium are shown in FIG. 5. 750 K. is the normal pretreatment temperature for this section using Cab-O-Sil silica. The yield falls with increasing pretreatment temperature, in agreement with the results on BDH silica, shown in Table 2. Since hydroxyl population is known to decrease at higher temperature, these results (and the effect of hydrating the catalyst, noted above) indicate that the ketene yield falls as the hydroxyl population decreases. The influence of temperature on the hydroxyl content of the surface and its influence on acetic acid uptakes, was therefore examined by gravimetry.

Calcination at different temperatures provides a method to change the population of hydroxyl groups on the silica surface. Estimates of the hydroxyl population changes on our Cab-O-Sil silica were obtained gravimetrically. The procedure is described below. A one-hour heat treatment at 423 K. was used to remove physically adsorbed water. The mass at the end of this low temperature treatment was used as the initial mass of the hydroxylated sample. Additional mass lost by heating to the (higher) desired calcination temperature for two hours was used to track OH population as a function of pretreatment temperature. Silica hydroxyl populations are well documented in the literature. Due to limitations in maximum operating temperature (873 K.) of our instrument, an assumption of zero hydroxyl population at the maximum operating temperature must be made (generally in the literature heating to a temperature near 1273 K. is used to obtain the zero point). Thus the absolute population of hydroxyl coverages from our samples may be underestimated, but the trends with hydration and pretreatment at temperatures below 873 K. will be unaffected. Gravimetric data clearly show that, once weakly bound water is removed, the hydroxyl population of the hydrated sample is higher than that of the untreated sample, and remains so at all pretreatment temperatures. The trends in the decrease of the OH population with temperature of these samples were in good agreement with published results.

The adsorption of acetic acid was also monitored gravimetrically on silica samples characterized by different hydroxyl populations. In these experiments, the silica sample was pretreated to the desired state, cooled to 323 K., and exposed to a flow of acetic acid in helium while monitoring the sample mass. At the end of the exposure the sample was purged with flowing helium until the sample mass reached a constant value. A two-hour purge was typically required. The mass at the end of the purge relative to that prior to the exposure may be taken to be representative of the strongly bound acetate species that give rise to TPD peaks upon subsequent heating. Comparison of the acetate coverages produced by acetic acid adsorption with the initial hydroxyl population of hydrated Cab-O-Sil samples pretreated at various temperatures demonstrated that the capacity for acetate formation was proportioned to the hydroxyl population for the hydrated samples, and thus that surface hydroxyls are the active sites for acetic acid adsorption and reaction to form ketene. The lower coverages of hydroxyls and of acetates on the untreated samples were also consistent with the very low activity of these samples demonstrated in FIG. 4, and again support the conclusion that surface hydroxyls are required.

The above results clearly demonstrate the efficacy of high surface area silicas for the production of ketenes from carboxylic acids. They further demonstrate that the surface area need not be limited to achieve selectivity, and that ketene yield increases with both silica surface area and hydroxyl population. Comparison of the dehydration behavior of $C_2$–$C_5$ carboxylic acids in both TPD and steady state catalysis experiments demonstrates that the selectivity of ketene production by this route does not exhibit a strong dependence on carbon number.

While there is shown and described herein certain specific structures embodying the invention, it will be manifest to those skilled in the art that various modifications and rearrangements of the parts maybe made without departing from the spirit and scope of the underlying inventive concept and that the same is not limited to the particular forms herein described.

What we claim:

1. A process for the production of ketenes comprising dehydration of a carboxylic acid in the presence of a catalyst which comprises silica having hydroxyl groups present on the surface at concentrations from about 0.5 to about 8/$nm^2$ and having a high surface area of at least 100 $m^2$/gram.

2. The process as claimed in claim 1, wherein the catalyst has a surface area from 120 to about 800 $m^2$/gram silica.

3. The process as claimed in claim 1, wherein the catalyst has a surface area from about 200 to about 800 $m^2$/gram silica.

4. The process as claimed in claim 1, wherein the catalyst has a surface area from 325 to about 800 $m^2$/gram silica.

5. The process as claimed in claim 1, wherein the catalyst has a surface area from 200 to about 380 $m^2$/gram silica.

6. The process as claimed in claim 1, wherein the ketenes are $C_2$–$C_{32}$ ketenes.

7. The process as claimed in claim 5, wherein the ketenes are $C_2$–$C_{22}$ ketenes.

8. The process as claimed in claim 1, wherein the ketenes are $C_2$–$C_5$ ketenes and have a selectivity of about 35 to about 90% at carboxylic acid conversions of about 30 to about 100%.

9. The process as claimed in claim 1, wherein said catalyst is hydrated.

10. The process as claimed in claim 9, wherein the catalyst has a surface area from 120 to about 800 $m^2$/gram silica.

11. The process as claimed in claim 10, wherein the ketenes are $C_2$–$C_{32}$ ketenes and have a selectivity of about 35 to about 90% at carboxylic acid conversions of about 30 to about 100%.

12. The process as claimed in claim 1, wherein the catalyst is added into a flow reactor that is operated at a temperature of at least about 600° K.

13. The process as claimed in claim 12, wherein the temperature is from about 700° K. to about 1000° K.

14. The process as claimed in claim 2, wherein the process is a one step catalytic process.

15. The process as claimed in claim 11, wherein after the catalyst is hydrated, said catalyst is heated to a temperature greater than the boiling point of water to achieve hydroxyl groups present on the surface of the catalyst at concentrations from about 0.5 to about 3/$nm^2$.

16. The process as claimed in claim 1, wherein said catalyst comprises protreating silica by hydration with water or steam to increase the amount of hydroxyl groups formed on the surface of said silica and then treating said silica with heat to a temperature above the boiling point of water to remove the desired amounts of hydroxyl groups and forming the resulting catalyst which comprises silica having a surface area of at least 100 $m^2$/gram.

17. The process as claimed in claim 4, wherein the ketenes are $C_2$–$C_{22}$-ketenes.

18. The process as claimed in claim 10, wherein the ketenes are $C_2$–$C_{22}$-ketenes and the catalyst has a surface area of about 200 to about 650 $m^2$/gram silica.

19. The process as claimed in claim 18, wherein the ketenes have a selectivity of about 35 to about 90% at carboxylic acid conversions of about 30 to about 100%.

* * * * *